United States Patent [19]

Shim

[11] B 3,991,019

[45] Nov. 9, 1976

[54] PROCESS FOR FORMING A FLAME RETARDANT ARTICLE AND ARTICLE THEREOF

[75] Inventor: K. S. Shim, Irvington, N.Y.

[73] Assignee: Stauffer Chemical Company, Westport, Conn.

[22] Filed: Mar. 12, 1975

[21] Appl. No.: 557,856

[44] Published under the second Trial Voluntary Protest Program on February 10, 1976 as document No. B 557,856.

Related U.S. Application Data

[62] Division of Ser. No. 460,399, April 12, 1974, Pat. No. 3,887,656.

[52] U.S. Cl. ............................ 260/2.5 AJ; 427/421; 427/428; 427/430 R; 260/DIG. 24
[51] Int. Cl.² .................... C08G 18/14; B05D 1/02; B05D 1/28
[58] Field of Search .............................. 260/2.5 AJ

[56] References Cited
UNITED STATES PATENTS

| | | |
|---|---|---|
| 3,033,887 | 5/1962 | Wadsworth et al. ................ 260/937 |
| 3,033,888 | 5/1962 | Wadsworth et al. ................ 260/937 |
| 3,257,480 | 6/1966 | Hechenbleikner et al. ......... 260/937 |
| 3,382,301 | 5/1968 | Hechenbleikner et al. ..... 260/2.5 AJ |

OTHER PUBLICATIONS

Pudovik et al., Chem. Abs., vol. 64 (1965) 159166.

*Primary Examiner*—H.S. Cockeram
*Attorney, Agent, or Firm*—Richard P. Fennelly

[57] ABSTRACT

Vinyl phosphonate esters are provided corresponding to the following formula:

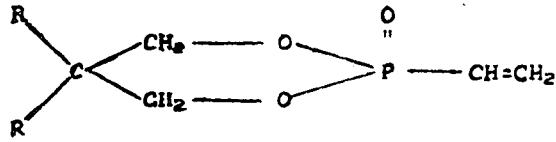

wherein R is the same or different and is a $C_1-C_{12}$ straight or branched aliphatic group, preferably a methyl group, or a phenyl group or a halo-substituted R group. A process for their production is also disclosed. These compounds are useful as flame retardants, particularly for polyurethane foams, thermoplastic and thermoset resins and cellulosic fibers.

13 Claims, No Drawings

PROCESS FOR FORMING A FLAME RETARDANT ARTICLE AND ARTICLE THEREOF

This is a division, of application Ser. No. 460,399 filed Apr. 12, 1974, now U.S. Pat. No. 3,887,656.

BACKGROUND OF THE INVENTION

This invention relates to vinyl phosphonate esters which are useful as flame retardants.

Recently, there has been a great deal of interest in providing effective flame retardants for normally flammable substrates. For example, much interest is being shown in compounds which may be added to polyurethane foam to act as flame retardants without destroying the desirable physical characteristics of the foam. In addition, the flame retarding of flammable substrates, such as textiles and thermoplastics, as well as polyurethane foam, for example, has become even more important as a result of recent governmental standards requiring that certain of these substrates be flame retarded.

In the past, however, the flame retarding of flammable substrates has presented some problems which have not been readily overcome. For example, one problem that arises results from the generally high processing temperatures (greater than 270°C.) required during the mixing and extruding of substrates such as thermoplastic fibers, like poly-(ethylene terephthalate) commonly referred to as Dacron. These high processing temperatures can cause the volatilization or thermal degradation of the therein incorporated flame retardant.

Moreover, aside from severe processing conditions, flammable substrates such as polyurethane foam, are generally subjected to ambient conditions which alone are sufficient to cause the volatilization or thermal degradation of a therein incorporated flame retardant. In addition to the loss of flame retardant activity, this degradation of the flame retardant material within the foam substrate may also result in the loss of many of the desired physical characteristics of the foam.

Regarding the flame retardant compounds themselves, while it is generally recognized that compounds which contain, for example, bromine have improved flame retardant capabilities, many of these compounds are unacceptable because of their volatility and thermal instability.

On the other hand, prior art flame retardant compounds have been developed which, while possessing the requisite thermal stability, do not possess sufficient flame retardant activity to allow for efficient use.

Accordingly, there is a need for flame retarding compounds, which while characterized by sufficient thermal stability, also possess efficient flame retardant capability.

TECHNICAL DISCLOSURE OF THE INVENTION

Therefore, it is one object of the present invention to provide novel vinyl phosphonate esters which are useful as flame retardants.

Another object of the present invention is to provide vinyl phosphonate esters which are characterized by excellent thermal stability and excellent flame retardant activity.

Still another object of this invention is to provide vinyl phosphonate esters which are particularly useful as flame retardants for polyurethane foam, thermoplastics and textiles.

A further object of this invention is to provide a novel process for the preparation of the novel vinyl phosphonate esters of the present invention.

The novel vinyl phosphonate esters of the present invention are represented according to the following general formula:

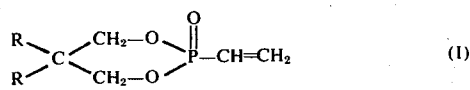

wherein R is a $C_1$–$C_{12}$ straight or branched aliphatic group, preferably a methyl group, or a phenyl group or halogenated derivatives of the foregoing R groups, preferably a bromo or chloro-substituted R group.

The novel vinylphosphonate esters of the present invention are formed by the following process.

The first step is the reaction of a compound of the formula

where R is defined as set forth above, with either phosphorus trichloride or phosphorus tribromide ($PX_3$, where X is Cl or Br) at a temperature between about 0°C and 100°C, preferably about 60°C, in a suitable organic solvent such as benzene, hexane, or chloroform. A preferred molar range of $PX_3$ to the compound shown in formula II is 4:1 to 1:1. The compound which is formed has the following formula:

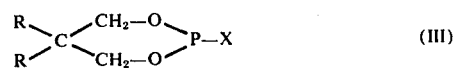

Compound III is then preferably reacted with an equimolar amount of ethylene oxide in hexane at a temperature of about 0° to 100°C, preferably about 40°C, to form the following compound:

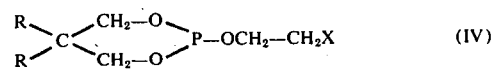

Compound IV is then treated to an Arbuzov rearrangement utilizing about 0.01 to 3%, by weight of compound IV, of a halide rearrangement catalyst, e.g., methyl iodide, at a temperature of above about 160°C, e.g., at about 190°C. Other rearrangement catalysts which can be used are the other $C_1$–$C_9$ alkyl halides, aryl halides, e.g., benzyl bromide or iodide, the alkali metal halides and iodine. The compound that results has the following formula:

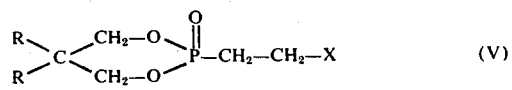

Compound V can be converted into the vinyl ester shown in formula I, above, by means of dehydrohalogenation, preferably by the reaction of compound V in the presence of a slight molar excess of base, such as, sodium acetate or triethylamine, and a suitable solvent, e.g., 1, 2-dichlorobenzene or tetrahydrofuran, at a temperature of about 100°–130°C, preferably about 110°–115°C.

As stated above, the vinyl phosphonate esters of the present invention are primarily intended for use as flame retardants for such normally flammable substrates as thermoplastics, textiles, and for flexible or rigid polyurethane foams.

Illustrative of some of thermoplastics which can be used with the novel flame retardant of this invention are polyesters, such as poly (ethylene terephthalate); cellulose esters, such as cellulose acetate and triacetate; cellulose ethers and other cellulosics such as rayon; polyamides, such as nylon; polyolefins such as polypropylene; polyethylene oxides, polypropylene oxides; acrylics and modacrylics, i.e., fibers based on acrylonitrile copolymers; saran fibers, i.e., fibers based on vinylidene chloride copolymers; spandex fibers, i.e., fibers based on a segmented polyurethane; vinyl fibers, i.e., fibers based on vinyl chloride copolymers and the like.

Of course, although the compounds of this invention are expecially well suited as flame retardants for thermoplastics and urethane foams, they also serve as efficient flame retardants in a wide variety of other flammable substrates such as paper, wood, polystyrene, polymethyl methacrylates, urethane coatings and elastomers and other natural and synthetic textiles such as cotton, wool, silk, sisal, jute, hemp, linen and the like.

The amount of vinyl phosphonate ester which is necessary to give satisfactory flame retardance in any particular flammable substrate system will generally vary over a wide range. Usually between about 1 to about 75% based upon the weight of the substrate of the flame retardant material is employed. Preferably between about 5 to about 15% is used. In general, any suitable known method of incorporating flame retardant materials may be utilized. For example, where thermoplastic fibers are the desired substrate, the flame retardants of the present invention may be blended with the molten polymers and extruded therewith to form the fibers. On the other hand, the flame retardant materials of this invention may be blended with the monomers prior to formation of the polymeric fiber material.

In addition, the flame retardants of the present invention may be added to textiles according to conventional procedures such as via aqueous or organic solutions which are either sprayed onto the textile or "padded on" by passing the textile through the solution while the latter is being held in a tank or other suitable container.

As also indicated above, the novel vinyl phosphonate flame retardants of this invention may also be incorporated in polyurethane foams. These polyurethane foams are well known in the art and are produced by the reaction of a di- or polyisocyanate and a di- or polyhydroxy (polyol) compound in the presence of a blowing agent and a catalyst. The foams can be made by any of the basic techniques used in foam formation, i.e., the prepolymer technique, the semi-prepolymer technique or the one-shot process. These techniques are well known and are described in the polyurethane art. A compound wherein R is a bromomethyl group has shown excellent flame retardancy in a flexible polyurethane foam.

Having generally described the invention, the following examples are given for purposes of illustration. It will be understood, however, that the invention is not limited to these examples but is susceptable to different modifications that will be recognized by one of ordinary skill in the art.

EXAMPLE 1

Formation of:

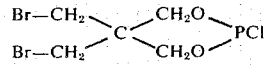

In a 2-liter flask containing 458g "1.75M" of dibromoneopentyl glycol and dry benzene (1000ml) was added dropwise phosphorus trichloride "460g, 3.34M" at 60°C. Upon completion of addition, solvent and excess phosphorus trichloride was stripped off to yield 540g (95%) of clear liquid product.

Boiling point: 120°C at 0.05mm Hg

Analysis: P = 9.4% (theory 9.5%); Br = 53.8% (theory 49.2%; Cl = 9.9% (theory 10.8%).

EXAMPLE 2

Formation of Dibromoneopentyl glycol chloroethylphosphite

In a 500 ml flask was placed the compound from Example 1 (133g: 0.41M) and dry hexane (150 ml). While stirring vigorously ethylene oxide was added through a sintered glass gas dispersing tube. The reaction temperature was maintained at 40°C using an ice bath since it was quite exothermic. Ethylene oxide was added until the reaction temperature began to drop. Yield = 97%.

EXAMPLE 3

Formation of the chloroethylphosphonate ester of dibromoneopentyl glycol

In a 250 ml flask was placed 200 g of the compound from Example 2 and 0.1g iodomethane. The resulting mixture was heated to 192°C and held at that temperature for 30 minutes to give 198g of clear liquid.

Analysis: P = 9.6% (theory 8.9%); Br = 37.9% (theory 43.3%); Cl = 8.6% (theory 9.6%).

EXAMPLE 4

Formation of the vinylphosphonate ester of dibromoneopentyl glycol

Into a 250 ml flask was placed the compound from Example 3 (92g: 0.25M), 0-dichlorobenzene (110 ml) and sodium acetate (30g: 0.35M). The resulting mixture was heated to 110° – 115°C and kept at that temperature over a period of 5 hours, after which the insoluble salts were separated through a filter and the organic layer was washed with water, dried over magnesium sulfate and stripped of solvent to give yellowish oil.

Analysis: P = 8.4% (Theory 8.6%); Br = 42.8% (Theory 44.6%).

EXAMPLE 5

The product from Example 4 was used in formulating a polyurethane foam utilizing the following neogents:

| REAGENT | AMOUNT (IN GRAMS) |
| --- | --- |
| Polyol (Voronol 3000) | 100 |
| Example 4 Product | 15 |
| Silicone L-520 Surfactant | 1.5 |

-continued

| REAGENT | AMOUNT (IN GRAMS) |
|---|---|
| Water | 3.6 |
| Amine Catalyst (A-1) | 0.12 |
| Dabco 33 LV | 0.35 |
| Blowing Agent (Cl$_3$CF) | 3.0 |
| DMF | 3.0 |
| T$_{10}$ (Stannous Octoate) | 0.60 |
| Toluene Diisocyanate | 45.8 |

The rise time of the foam was 120 seconds at ambient temperature. The foam that was produced weighed 6.393, had a density of 2.03 lbs/ft and had an average air flow of 4.3 ft 3/min.

When three samples of the foam were tested for flame retardancy using ASTM-1692 the samples self-extinguished between 80 and 95 seconds after 60–70 mm of foam had burned. The average burn rate was 0.72 mm/sec. for all three samples.

A number of compounds having the following structural formula:

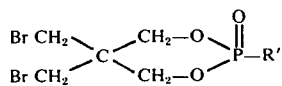

where R' is defined in the Table below were incorporated in the polyurethane foam formulation set forth above and were tested for flame retardancy. The table sets forth the burn rate:

| R' | Average Burn Rate (mm sec) |
|---|---|
| OCH$_2$CH=CH$_2$ | 1.30 |
| N(CH$_3$)$_2$ | 0.73 |
| OCH$_2$CH$_2$Cl | 0.70 |

What is claimed is:
1. A process for forming a flame retardant article which comprises the addition to a normally flammable substrate of an effective amount of at least one compound having the formula:

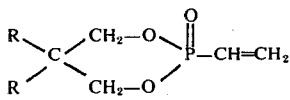

wherein R is selected from the group consisting of the straight and branched C$_1$–C$_{12}$ alkyl groups, the phenyl group, and bromo and chloro substituted C$_1$–C$_{12}$ alkyl groups, and the bromo and chloro substituted phenyl groups to confer flame retardancy on the substrate.

2. A process as set forth in claim 1 wherein the amount of compound which is added ranges from about 1 to 75% by weight of the substrate.

3. A process as set forth in claim 1 wherein the amount of compound which is added ranges from about 5 to about 15% by weight of the substrate.

4. A process as set forth in claim 1 wherein the substrate is a polyurethane foam.

5. A process as set forth in claim 4 wherein R is a bromomethyl group.

6. A process as claimed in claim 1 wherein the substrate is a thermoplastic resin.

7. A process as claimed in claim 1 wherein the substrate is a textile.

8. A flame retardant article comprising a substrate and an effective amount of flame retarding of a compound having the formula:

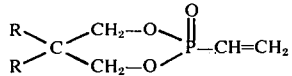

wherein R is selected from the group consisting of the straight and branched C$_1$–C$_{12}$ alkyl groups, the phenyl group, the bromo and chloro substituted C$_1$–C$_{12}$ alkyl groups, and the bromo and chloro substituted phenyl groups.

9. An article as claimed in claim 8 wherein the article contains about 1 to about 75% by weight of the compound based on the weight of the substrate.

10. An article as claimed in claim 8 wherein the article contains about 5 to about 15% by weight of the compound based on the weight of the substrate.

11. An article as claimed in claim 8 wherein the substrate is a polyurethane foam.

12. An article as claimed in claim 8 wherein the substrate is a thermoplastic resin.

13. An article as claimed in claim 8 wherein the substrate is a textile.

* * * * *